United States Patent [19]

Orcutt

[11] 4,202,883
[45] May 13, 1980

[54] VACCINE FOR TYZZER'S DISEASE IN RABBITS

[75] Inventor: Roger P. Orcutt, North Andover, Mass.

[73] Assignee: The Charles River Breeding Laboratories, Inc., N. Wilmington, Mass.

[21] Appl. No.: 38,012

[22] Filed: May 10, 1979

[51] Int. Cl.$^2$ .............................................. A61K 39/02
[52] U.S. Cl. ...................................................... 424/92
[58] Field of Search ......................................... 424/92

[56] References Cited

PUBLICATIONS

Fujiwarak et al., Comptesrendes Soc. Biol., 1977 (171)(3): 710-714, Thymus-Dependent Immunity to Tyzzer's Disease in the Mouse.

Prescott, J. F., Vet. Rec. 100(14): 285-286, Apr. 1977, Tyzzer's Disease Caused by *Bacillus piliformis* in Rabbits in Britain.

Ganaway, Jr. et al., J. Wildl. Dis. 12(4): 545-549, Oct. 1976 Tyzzer's Disease in Free-Living Cottontail Rabbits in Maryland (*Bacillus piliformis*).

Cutlip, R. C., Vet. Pathol. (VTPHA) 9(1): 1972, 87-88 Tyzzer's Disease in Rabbits.

Cutlip, R. C. et al., Lab. Anim. Sci. (LBASA) 21(3): 1971, 356-361, An Epizootic of Tyzzer's Disease in Rabbits.

Yamada et al., Jap. J. Exp. Med. 39(5): 505-18 (1969) Tyzzer's Disease Syndrome in Laboratory Rats Treated with Adrenocorticotropic Hormone.

Ganaway, J. R. et al., Infect. Immun. (INFIB) 3(3): 1971, 429-437 Tyzzer's Disease of Rabbits Isolation and Propagation of *Bacillus piliformis* in Embryonated Eggs.

Fries A. S., Lab Anim. (LBANA) 13(1)(1979) 37-42, Studies on Tyzzer's Disease A Long-Term Study of the Humoral Antibody Response in Mice, Rats and/Rabbits.

Fries, A. S., Lab. Anim. 11(2): 69-73, Apr. 1977, Studies on Tyzzer's Disease Immunofluoroscope for Detection of *Bacillus piliformis* and for Demonstration and Determination of Antibodies to it in Sera from Mice and Rabbits.

*Primary Examiner*—Shep K. Rose
*Attorney, Agent, or Firm*—Morse, Altman, Oates & Bello

[57] ABSTRACT

A vaccine for Tyzzer's disease in rabbits is produced from inactivated hepatic or intestinal tissue of immunosuppressed rodents which have been infected with *Bacillus piliformis*.

10 Claims, No Drawings

VACCINE FOR TYZZER'S DISEASE IN RABBITS

BACKGROUND OF THE INVENTION

1. Field of the Invention

The present invention relates to Tyzzer's disease of rabbits and, more particularly, to a vaccine for Tyzzer's disease in rabbits and a method for its production.

2. The Prior Art

In 1917, Ernest Edward Tyzzer of the Harvard University Medical School described a disease in mice that has borne his name since (Tyzzer, E. E., 1917, A Fatal Disease of the Japanese Waltzing Mouse Caused by a Spore-Bearing Bacillus (Bacillus piliformis, N. SP.), J. Med. Res. 37: 307–338). Tyzzer's disease subsequently was discovered in rats (Jonas, A. M., D. H. Percy, and J. Craft, 1970, Tyzzer's Disease in the Rat, Its Possible Relationship with Megaloileitis, Arch. Pathol. 90: 516–528), gerbils (Carter, G. R., D. L. Whitenack and L. A. Julius, 1969, Natural Tyzzer's Disease in Mongolian Gerbils [Meriones unguiculatus], Lab. Anim. Care 19: 948–951), monkeys (Niven, J. S. F. 1968, Tyzzer's Disease in Laboratory Animals, Z. Vers. 10: 168–174), and rabbits (Allen, A. M., J. R. Ganaway, T. D. Moore, and R. F. Kinard, 1965, Tyzzer's Disease Syndrome in Laboratory Rabbits, Amer. J. Pathol 46: 859–881). In each of these species, the etiological agent, originally named Bacillus piliformis by Tyzzer, was described as a long, slender bacterium that produces spores, is Gram-negative, and cannot be grown in or on cell-free media. Nevertheless, Ganaway et al. were able to isolate the organism from rabbits by inoculation of infected liver homogenates into the yolk sac of 7-day-old embryonated chicken eggs (Ganaway, J. R., A. M. Allen, and T. D. Moore, 1971, Tyzzer's Disease of Rabbits: Isolation and Propagation of Bacillus piliformis (Tyzzer) in Embryonated Eggs, Inf. and Immun. 3: 429–437), a procedure similar to the procedure used by Craigie to isolate B. Piliformis from mice (Cragie, J. 1966. Bacillus piliformis [Tyzzer] and Tyzzer's Disease of the Laboratory Mouse, I. Propagation of the Organism in Embryonated Eggs, Proc. Roy. Soc, Edinburgh, Sect. B. Biol. 165: 35–60).

BRIEF SUMMARY OF THE INVENTION

The object of the present invention is to provide, as a vaccine for Tyzzer's disease in rabbits, a homogenate of the inactivated hepatic or intestinal tissue of immunosuppressed gnotobiotic or non-isolator maintained rodents which have been infected with Bacillus piliformis. Preferably the vaccine is produced by the steps of infecting gnotobiotic rodents by subjection to a yolk sack epithelium culture of Bacillus piliformis in an otherwise sterile medium, immunosuppressing these rodents by subjection to a corticosteroid, thereby causing the establishment and growth of Bacillus piliformis lesions in the tissues of the liver and intestines, dispersing this tissue in a vehicle to provide an active medium, and inactivating this medium by addition of an aldehyde fixing agent. With respect to the final product by total weight, the concentration of the tissue ranges from 0.1 to 50% and the concentration of the fixing agent ranges from 0.1 to 25%. It has been found that a vaccine of the foregoing type contains a sufficiently heavy concentration of Bacillus piliformis bacterin for immunological effectiveness in rabbits.

DETAILED EXAMPLE OF THE MATERIALS AND METHODS OF THE PREFERRED EMBODIMENT

Animals

The rabbits utilized herein were of the type sold by the Charles River Breeding Laboratories, Inc. under the trade designation COBS (NZW) BR strain; and the gnotobiotic mice utilized herein were of the type sold by the Charles River Breeding Laboratories, Inc. under the trade designation CD-1 (ICR) GN strain.

Vaccine Production

A ten percent weight/volume aqueous homogenate of infected yolk sac epithelia was prepared according to the method of Ganaway, supra, and 0.1 cc quantities were injected intraperitoneally or intravenously into weanling gnotobiotic mice. The mice were then cortisonized by subcutaneous (or intraperitoneal) injection of 0.1 cc of a 25 milligram/cc preparation of cortisone acetate. Cortisonization in this manner was continued twice a week until death. The livers then were excised and homogenized in an aqueous phosphate buffered saline vehicle (PBS) and formalin was added to produce a final weight/volume concentration of 20 percent liver tissue and 1.0 percent formalin. This procedure was performed in the morning and the vaccine was allowed to remain at room temperature for the ramainder of the day, or approximately six hours. It was refrigerated for one week at 4° C., tested for sterility and then stored at 4° C. until use. More generally, the concentration of the infected yolk sack epithelial tissue is not critical, the concentration of the cortisone acetate is not critical, the phosphate buffered saline vehicle can be any buffer diluent having a pH ranging from 3 to 10, and best results are achieved when the concentration of the liver tissue ranges from 0.1 to 50% and the concentration of the formalin ranges from 0.1 to 25%.

Sterility Testing

Both formalized and unformalized control liver preparations were maintained at 4° C. for one week and then assayed for viability. Aliquotes of each were centrifuged at 8,000 times gravity for ten minutes and the pellets were washed three times in their original volumes of PBS. The final suspensions then were inoculated into 7-day-old embryonated chicken eggs (0.5 cc/egg) and onto two sheep blood agar plates (0.1 cc/plate). One blood agar plate was incubated aerobically at 35° C. and one anaerobically at 35° C. Eggs were read after one week of incubation at 37° C. while plates were read daily for one week.

Vaccine Efficacy Testing

The rabbits were vaccinated by a series of three injections spaced two weeks apart, each consisting of 2 cc of vaccine administered subcutaneously in the cervical region of the back (or intraperitoneally). One month after the last injection, each vaccinated and each unvaccinated control rabbit was challenged gavage with 5 cc of a 10 percent suspension of caecal contents obtained from a rabbit that had died of Tyzzer's disease. The animals then were placed on sulfaquinozaline-treated drinking water (1.5 g/gal.), were given intramuscular injections of cortisone acetate (50 mg/kg of body weight), and were observed for a period of one month.

Results

Eight rabbits were vaccinated and then challenged two weeks after their last injection along with three nonvaccinated control animals. As indicated in the following table, all vaccinated rabbits remained totally asymptomatic while all three nonvaccinated animals died of typical Tyzzer's disease within ten days. The vaccinated rabbits then were euthanized via $CO_2$ asphyxiation 30 days post challenge and were necropsied. No signs of Tyzzer's disease were found.

TABLE

Efficacy of Rabbit Tyzzer's Vaccine

| Number | Rabbit Sex | Weight (kg) | Treatment | Results Up to 30 Days Post Challenge |
|---|---|---|---|---|
| 1 | F | 1.8 | Vaccinated | Unaffected |
| 2 | M | 3.0 | Vaccinated | Unaffected |
| 3 | F | 3.0 | Vaccinated | Unaffected |
| 4 | M | 3.2 | Vaccinated | Unaffected |
| 5 | M | 3.6 | Vaccinated | Unaffected |
| 6 | M | 4.1 | Vaccinated | Unaffected |
| 7 | F | 4.3 | Vaccinated | Unaffected |
| 8 | M | 4.3 | Vaccinated | Unaffected |
| 9 | M | 1.8 | Nonvaccinated | Died of Tyzzer's Disease |
| 10 | M | 2.3 | Nonvaccinated | Died of Tyzzer's Disease |
| 11 | M | 2.5 | Nonvaccinated | Died of Tyzzer's Disease |

CONCLUSION

Although Tyzzer's disease in rabbits was first recognized in 1965, (Allen et al. supra), its etiological agent was not isolated until six years later (Ganaway et al. supra) The present invention has involved isolating a rabbit strain of *Bacillus piliformis* from a colony or rabbits experiencing a natural epizootic of Tyzer's disease. The isolate then was passed into germfree mice which died within three weeks of infection. The livers of these animals demonstrated coalescing lesions due to the proliferation of *Bacillus piliformis* and were used to prepare the formalized bacterin of the present invention. This vaccine has been shown to protect susceptible rabbits against a lethal challenge of *Bacillus piliformis*. Since certain changes may be made in the foregoing disclosure without departing from the invention herein, it is intended that all matter described in the foregoing specification be interpreted in an illustrative and not in a limiting sense.

What is claimed is:

1. A vaccine for Tyzzer's disease in rabbits, said vaccine comprising the reaction product, in an aqueous vehicle, of a fixing agent and hepatic or intestinal tissue from immunosuppressed rodents infected with *Bacillus piliformis*.

2. The vaccine of claim 1, wherein by total weight of said vaccine, said fixing agent ranges from 0.1 to 25% and said tissue ranges from 0.1 to 50%.

3. A method of producing a vaccine for Tyzzer's disease, said method comprising the steps of:
   (a) injecting into living germfree or nonisolator maintained rodents, an aqueous homogenate of chicken yolk sac epithelia infected with *Bacillus piliformis*;
   (b) subjecting or not subjecting said rodents to an immunosuppressant until death thereof;
   (c) excising hepatic or intestinal tissue from said rodents;
   (d) dispersing said hepatic or intestinal tissue in a buffered aqueous diluent; and
   (e) adding a fixing agent to inactivate said *Bacillus piliformis*.

4. The method of claim 3 wherein said immunosuppressant is a corticosteroid.

5. The method of claim 3 wherein said immunosuppressant is a cortisone compound.

6. The method of claim 3 wherein said diluent ranges in pH from 3 to 10.

7. The method of claim 3 wherein said fixing agent is 37% aqueous solution of formaldehyde.

8. The method of claim 3 wherein said fixing agent ranges from 0.1 to 25% by total weight of said vaccine.

9. The method of claim 3 wherein said tissue ranges from 0.1 to 50% by total weight of said vaccine.

10. The method of claim 3 wherein, by total weight of said vaccine, said fixing agent ranges from 0.1 to 25% and said tissue ranges from 0.1 to 50%.

* * * * *